United States Patent [19]

Chern et al.

[11] Patent Number: 5,158,953

[45] Date of Patent: Oct. 27, 1992

[54] 2-SUBSTITUTED METHYL-2,3-DIHYDROIMIDAZO[1,2-C]QUINAZOLIN-5(6H)-ONES (THIONES), THE PREPARATION AND USE THEREOF

[75] Inventors: Ji-wang Chern; Chia-Yang Shiau; Mao-Hsiung Yen; Guan-Yu Lu, all of Taipei, Taiwan

[73] Assignee: National Science Council, Taipei, Taiwan

[21] Appl. No.: 744,534

[22] Filed: Aug. 13, 1991

[51] Int. Cl.$^5$ .................. A61K 31/505; C07D 487/04
[52] U.S. Cl. ..................... 514/267; 544/230; 544/250; 544/286; 558/417; 558/418
[58] Field of Search .................. 544/250, 230; 514/267

[56] References Cited

U.S. PATENT DOCUMENTS

| | | | |
|---|---|---|---|
| 3,511,836 | 5/1970 | Hans-Jurgen | 544/119 |
| 4,335,127 | 6/1982 | Vandenberk et al. | 544/285 |
| 4,585,772 | 4/1986 | Junge et al. | 544/250 |

OTHER PUBLICATIONS

Klein et al, *Chemical Abstracts*, vol. 110, No. 75431 (1989), (Abstract for Chem.-Ztg. 111, p. 373 (1989)).

Jun-ichi Imagawa, et al. Article entitled "Further Evaluation of the Selectivity of a Novel Antihypertensive Agent, SGB-1534, For Peripheral $\alpha_1$-Adrenoceptors in the Spinally Anesthetized Dog," *Eur. J. Pharmacol.*, 131 257-264 (1986).

Imagawa et al., Chemical Abstracts, 106:43742t, (1987).

*Primary Examiner*—Mukund J. Shah
*Assistant Examiner*—F. Bernhardt
*Attorney, Agent, or Firm*—Winstead Sechrest & Minick

[57] ABSTRACT

The present invention provides a novel series of 2-substituted methyl-2,3-dihydroimidazo[1,2-c]quinazolin-5(6H)-ones (-thiones) compounds. These compounds are found useful as an active ingredient for the prophylaxis and treatment of hypertension.

12 Claims, 3 Drawing Sheets

2-SUBSTITUTED METHYL-2,3-DIHYDROIMIDAZO[1,2-C]QUINAZOLIN-5(6H)-ONES (THIONES), THE PREPARATION AND USE THEREOF

TECHNICAL FIELD OF THE INVENTION

The present invention relates to new and useful imidazo[1,2-c]quinazolinone derivatives, especially relates to 2-substituted methyl-2,3-dihydroimidazo[1,2-c]quinazolin-5(6H)-ones (-thiones).

BACKGROUND OF THE INVENTION

Quinazoline ring system constituting a class of antihypertensive agents is well known in the art. Prazosin disclosed in U.S. Pat. No. 3,511,836, a 2-substituted quinazoline derivative, has been proven effective in the clinic acting as an $\alpha_1$-adrenoceptor antagonist.

U.S. Pat. No. 4,335,127 discloses 3-substituted quinazolines such as ketanserin, thioketanserin which have been found being potent serotonin-antagonists.

In an article entitled "Further Evaluation of the Selectivity of a Novel Antihypertensive agent, SGB-1534, for Peripheral $\alpha$1-adrenoceptors in the Spinally Anesthetized Dog" *Eur. J. Pharmacol.* 1986, 131, 257–264, Junichi Imagawa et al. disclose SGB-1534, a 3-substituted quinazoline derivative, which also have been proven to have antihypertensive activities by an $\alpha_1$-adrenoceptor antagonist.

As a result of an extensive investigations to develop a more potent and clinically effective antihypertensive agent, a novel series of imidazo[1,2-c]quinazolinone derivatives, 2-substituted methyl-2,3-dihydroimidazo[1,2-c]quinazolin-5(6H)-ones (-thiones), have been newly synthesized in the present invention.

Accordingly, one object of the present invention is to provide new and useful 2-substituted methyl-2,3-dihydroimidazo[1,2-c]quinazolin-5(6H)-ones (-thiones) and pharmaceutically acceptable salts thereof.

Another object of the present invention is to provide a process for preparing the 2-substituted methyl-2,3-dihydroimidazo[1,2-c]quinazolin-5(6H)-ones (-thiones) and pharmaceutically acceptable salts thereof.

A further object of the present invention is to provide a pharmaceutical composition containing, as an active ingredient, the 2-substituted methyl-2,3-dihydroimidazo[1,2-c]quinazolin-5(6H)-ones (-thiones) or a pharmaceutically acceptable salt thereof.

Still another object of the present invention is to provide a method for the treatment of high blood pressure comprising administrating to a mammal in need of said treatment an effective amount of the 2-substituted methyl-2,3-dihydroimidazo-[1,2-c]quinazolin-5(6H)-ones (-thiones) or a pharmaceutically acceptable salt thereof.

SUMMARY OF THE INVENTION

The present invention provide a novel series of 2-substituted methyl-2,3-dihydroimidazo[1,2-c]quinazolin-5(6H)-ones (-thiones) compounds having the formula:

wherein:
X is O or S;
$R_1$ is hydrogen, lower alkyl, aryl or aryl(lower alkyl);
$R_2$ is hydrogen, lower alkyl, aryl or aryl(lower alkyl);
or $R_1$ and $R_2$ together represent alkylene of 4 to 10 carbon atoms or wherein $R_5$ represents (a) 2-(2-hydroxyethoxy)ethyl; (b) pyrimidinyl; (c) a 2-, 3- or 4-pyridinyl optionally substituted by one or two substituents each independently selected from the group consisting of $C_1$–$C_4$ alkyl; and (d) benzoyl, benzyl, phenyl and diphenylmethyl optionally substituted by one or two substituents selected from the group consisting of halogen atom, methoxy, trifluoromethyl, $C_1$–$C_4$ alkyl, nitro, acetyl, and cyano; and (i) $R_6$ and $R_7$ together represent alkylene of 4 to 6 carbon atoms or (ii)

or (iii) when $R_6$ represents hydrogen atom or hydroxy, $R_7$ represents (a) pyrimidine; (b) a 2-, 3- or 4-pyridinyl optionally substituted by one or two substituents each independently selected from the group consisting of $C_1$–$C_4$ alkyl; and (c) benzoyl, benzyl, phenyl and diphenylmethyl optionally substituted by one or two substituents selected from the group consisting of halogen atom, methoxy, trifluoromethyl, $C_1$–$C_4$ alkyl, nitro, acetyl, and cyano; $R_3$ is halogen, hydrogen, alkyl, trifluoromethyl, or lower alkoxy; and $R_4$ is halogen, hydrogen, alkyl, trifluoromethyl, or lower alkoxy; and pharmaceutically acceptable salts thereof.

The compounds represented by formula (I) include racemic mixture of optically active compounds and optically pure R and S stereoisomers.

The compounds of formula (I) and the salts thereof are excellent in antihypertensive activity and are, therefore, useful as pharmaceuticals.

DETAILED DESCRIPTION OF THE PREFERRED EMBODIMENTS

As used in the foregoing definitions term "lower alkyl" is meant to include straight and branched hydrocarbon radicals having from 1 to 6 carbon atoms; the term "alkylene" comprises straight and branched alkylene; and the term "halogen" refers to fluorine, chlorine and bromine.

The pharmacologically allowable salts include inorganic acid salts such as hydrochlorides, sulfates, hydrobromides, perchlorates and nitrates; and organic acid salts such as oxalates, maleates, fumarates, succonates and methanesulfonates.

Preferred compounds within the scope of formula (I) are 2-(4-phenyl-1-piperazinyl)-methyl-2,3-dihydroimidazo[1,2-c]quinazolin-5(6H)-one; 2-(4-phenyl-1-piperazinyl)-methyl-2,3-dihydroimidazo[1,2-c]quinazolin-5(6H)-thione; and 2-[4-(1-phenyl)-piperazinyl]methyl-8,9-dimethoxy-2,3-dihydro-imidazo[1,2-c]quinazolin-5(6H)-one. Among them 2-(4-phenyl-1-piperazinyl)-methyl-2,3-dihydroimidazo[1,2-c]-quinazolin-5(6H)-one is most preferable.

A process suitable for preparing the compounds of formula (I) comprises (a) reacting a compound having the formula (II)

wherein $R_3$ and $R_4$ have the same meanings as defined above, with a compound of the formula (III)

wherein X has the same meaning as defined above, (b) reacting the resulting compound having the formula (IV)

wherein $R_3$ and $R_4$ have the same meanings as defined above, with a base, (c) reacting the resulting compound having the formula (V)

wherein $R_3$ and $R_4$ have the same meanings as defined above, with N-halosuccimide or halogen, and (d) reacting the resulting compound having the formula (VI)

wherein $R_3$ and $R_4$ have the same meanings as defined above; Y represents halogen, with a compound of formula (VII)

(VIII)

or (IX)

wherein $R_1$, $R_2$, $R_5$, $R_6$ and $R_7$ have the same meanings as defined above, as a suitable side chain.

The reaction between compound (VI) and the appropriate side chain can be carried out in the presence of a suitable base in a suitable solvent.

Examples of the suitable base which can be used in the reaction include inorganic bases such as sodium carbonate, potassium carbonate, sodium hydrocarbonate, potassium hydrocarbonate, silver carbonate, cesium carbonate and the like; and the organic bases such as triethyl amine, pyridine, N,N-dimethylaniline, N-methylmorpholine, DBU, DBN and the like. An excess amount of the side chain used in the reaction can also function as a base.

The reaction can be carried out in any inert solvent which does not adversely affect the reaction. Examples of these inert solvent include ethers such as diethyl ether, tetrahydrofuran, dioxane, diglyme, etc.; ketones such as MIBK; and acetonitrile. There is no particular limit on the reaction temperature, preferably the reaction temperature is ranging from 0° to 200° C. Generally, the reaction is completed in about 1 to 72 hours.

In the step a), the condensation reaction between the compound of formula (II) and the compound of formula (III) can be carried out neatly or in a suitable solvent. Any solvent which does not interfer with the reactant can be use in the reaction. Examples of suitable solvent include chloroform, dichloromethane, ether, etc. The reaction generally is performed at room temperature and completed in two days.

The ring closure of compound (IV) in the step b) is carried out in the presence of a base such as ammonia water, triethylamine, pyridine, DBN, DBU and the like. The reaction can be carried out in the absence or presence of a solvent. Any inert solvent which does not adversely influence the reaction can be used. Examples of the solvent include water; alcohols such as methanol, ethanol, etc.; ethers such as diethyl ether, tetrahydrofuran, etc. The reaction generally is completed in about 15 minutes.

The halocyclization of compound (V) in the step c) can be carried out in the presence of N-halosuccimide or halogen in the absence or presence of a suitable solvent. Any solvents which does not influence the reaction can be used such as water, alcohols, ether and dimethylsulfoxide. The reaction usually is carried out at room temperature and completed in about 30 minutes.

The compounds of formula (I) and the salts thereof are excellent in antihypertensive activity and are, therefore, useful in the prophylaxis and treatment of hypertension.

The potency of the subject compounds as hypertension-antagonists is clearly evidenced by the results obtained in the following tests wherein the antihypertensive activity of 2-(4-phenyl-1-piperazinyl)methyl-2,3-dihydroimidazo[1,2-c]quinazolin-5(6H)-one, synthesized in the following Example 4, is examined.

ANTIHYPERTENSIVE ACTIVITY

Adult cats of either sex, 2-3 Kg, anesthetized with pentobarbital sodium (30 mg/Kg i.p.) were used. The trachea was intubated to provide artificial respiration with air by means of a Harvard respirator (respiration rate=16-20/min and colume=40-50 ml/stroke). Both femoral artery and vein were cannulated with PE 150 to monitor blood pressure and for drug administration respectively. Body temperature was maintained at 37.5° C. with a heating pad and monitored with a rectal thermometer. Blood pressure was measured with a Statham P23D pressure transducer via a polyethylene cannula conducted to a right femoral artery. Heart rate was measured through a Grass Model 7B tachograph preamplifier triggered by the pulses of arterial blood pressure. All data were recorded on a Grass Model 7B polygraph.

1. Hypotensive action of i.v. 2-(4-phenyl-1-piperazinyl)-methyl-2,3-dihydroimidazo[1,2-c]quinazolin-5(6H)-one (Example 4) in cats.

Figure 1:
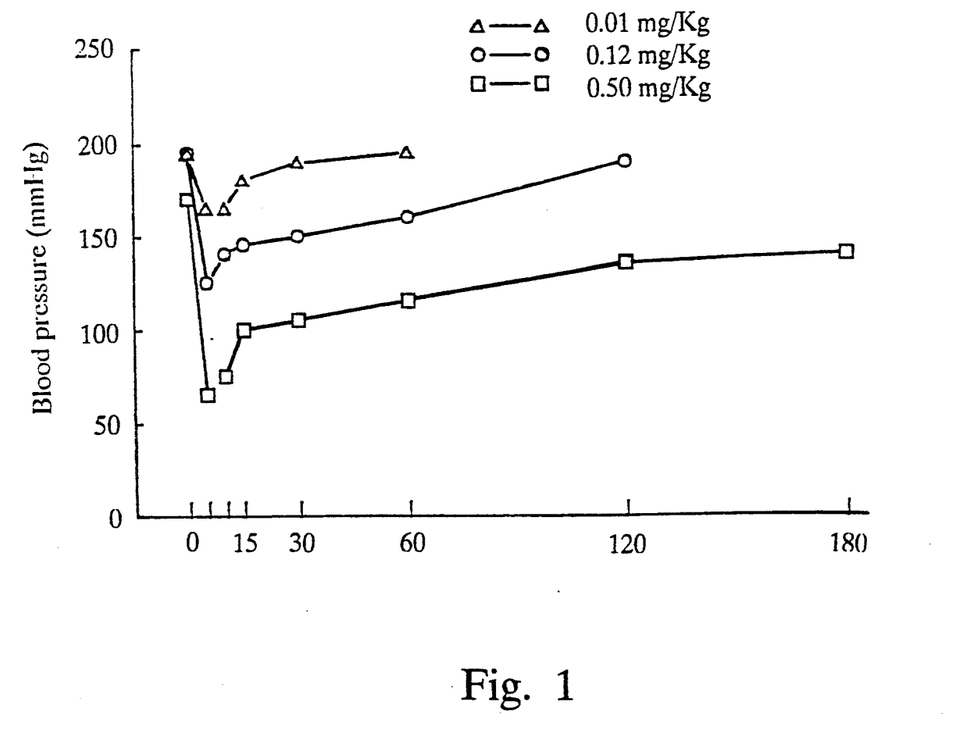
FIG. 1 is a does-response plot of 2-(4-phenyl-1-piperazinyl)methyl-2,3-dihydroimidazo[1,2-c]-quinazoline-5(6H)-one (Example 4) on blood pressure in 5 cats.

FIG. 1. showed the dose-response curves of the maximum changes in SBP, DBP and heart rate after i.v. administration of Example 4 compound in cats. Example 4 compound (10 μg to 1 mg/kg) decreased both SBP and DBP, and changed in heart rate (HR) biphasically (initially increased, then decreased) in a dose-dependent manner, $ED_{50}$ of lowing blood pressure of Example 4 compound was 250 μg/Kg.

Figure 2:
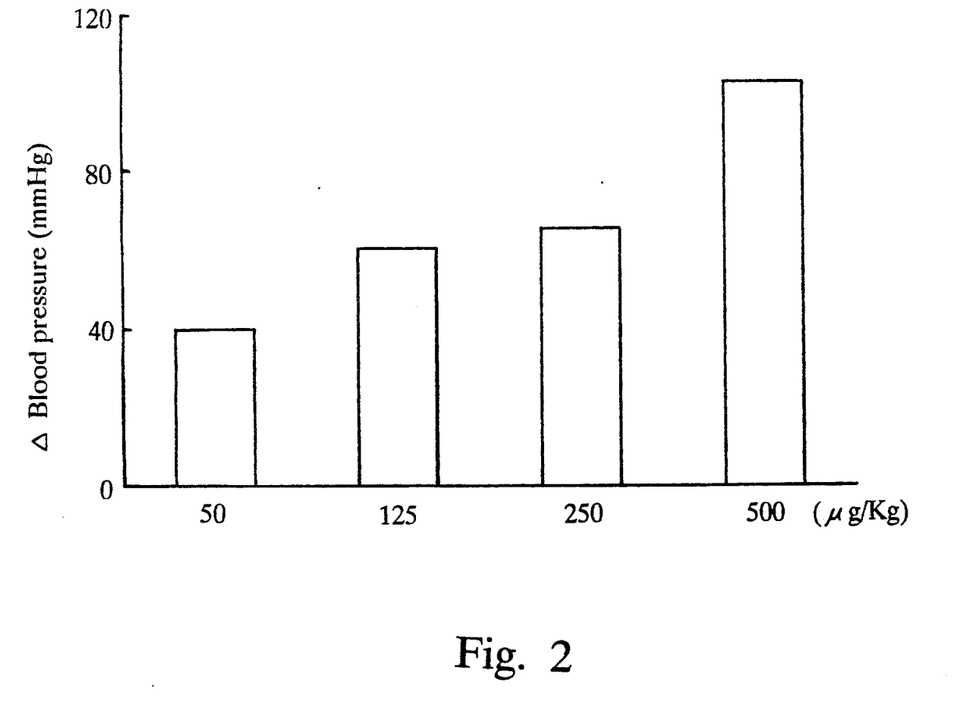
FIG. 2 is a time-course of various doeses of Example 4 compound on blood pressure in cats.

The time course of the hypotensive action of Example 4 compound administration i.v. in anesthetized cat was shown in FIG. 2. The solvent (50% DM50) had no significant action on B.P. or H.R. However, Example 4 compound (250 μg/Kg) decreased B.P. immediately and reached maximally at 5-10 minutes, and the duration of action was about 4 hours.

Figure 3:
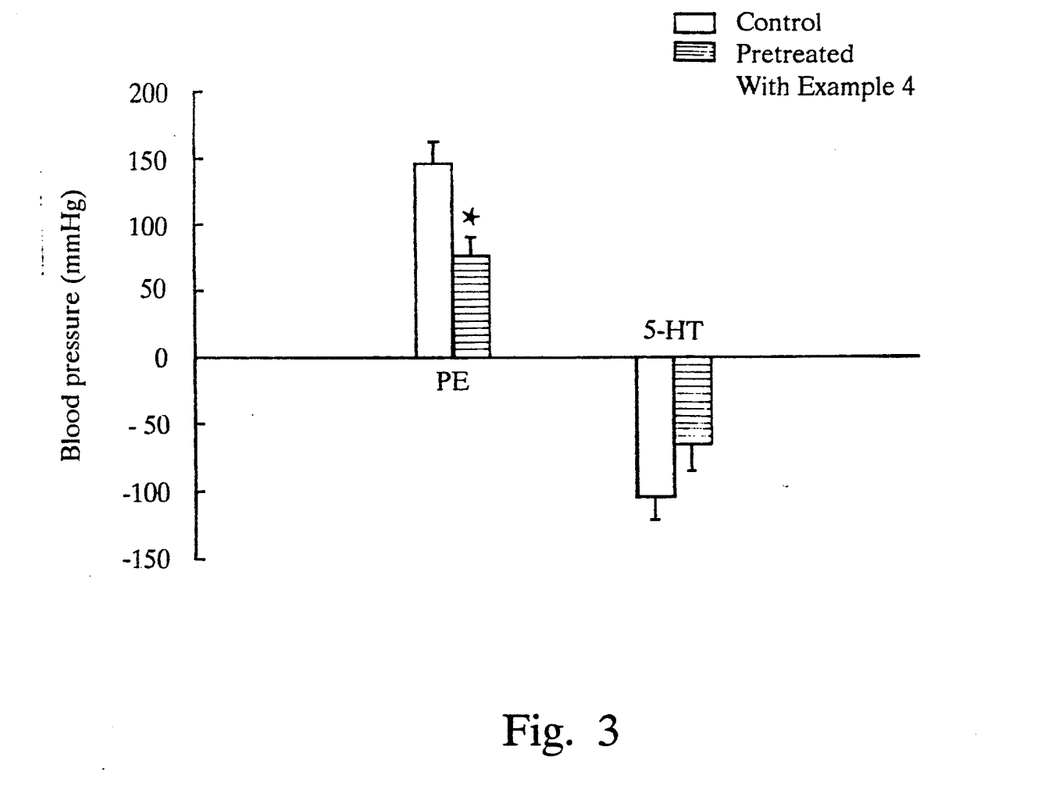
FIG. 3 is a plot showing antagonistic effect of Example 4 compound (0.25 mg/kg) on blood pressures induced by phenylephrine (0.015 mg/kg) or serotonin (0.020 mg/kg).

2. Effects of pretreated with Example 4 compound on blood pressure induced by PE and 5-HT in cats. The data as shown in FIG. 3 demonstrated that Example 4 compound in doses of $ED_{50}$ significantly antagonized the blood pressure response to PE ($p<0.02$) but no effect on 5-HT ($p>0.05$). Results suggested that the imidazo[1,2-c]quinazolinone derivatives of the general formula (I) be a novel $\alpha_1$-adrenoreceptor antagonist.

Compounds of the invention may be formulated for use in a pharmaceutical composition. Accordingly, in a further aspect of the invention, there is provided a pharmaceutical composition which comprises a compound of formula (I) or pharmaceutically acceptable salt thereof together with a pharmaceutically acceptable carrier or excipient.

A composition which may be administered by the oral route to humans may be compounded in the form of a syrup, tablet or capsule. When the composition is in the form of a tablet, any pharmaceutical carrier suitable for formulating such as solid compositions may be used, for example magnesium sterate, starch, lactose, glucose and flavor. The compounds may also be presented with a sterile liquid carrier for injection.

The present invention is now illustrated in greater detail by the following Examples but it should be understood that the present invention is not limited thereto.

EXAMPLE 1

2-(3-allylureido)benzonitrile

A mixture of anthranilonitrile (10.0 g, 85 mmol) and allyl isocyanate (7.5 mL, 85 mmol) was slightly heated to dissolve. The resulting solution was allowed to stir at room temperature for two days. The solid was collected by filtration and washed with ether (10 mL) to give 14.4 g (100%) of 2-(3-allylureido)benzonitrile. An analytical sample was recrystallized from ethanol. IR (KBr): 3331, 3263, 2226 (CN), 1639 $cm^{-1}$. $^1H$ NMR (300 MHz, DMSO-d6): δ3.74 (p, 2H, $CH_2$), 5.09 (q, 1H, =CH), 5.17 (q, 1H, =CH), 5.86 (m, 1H, CH), 7.09 (t, 2H, Ar—H), 7.56 (t, 1H, Ar—H), 7.67 (d, 1H, Ar—H), 8.43 (d, 1H, Ar—H), 7.65 (d, 1H, NH), 8.54 (s, 1H, NH). $^{13}C$ NMR (75 MHz, DMSO-d6): δ41.47, 101.00, 114.97, 116.99, 120.61, 120.73, 122.22, 132.96, 133.83, 135.69, 142.66, 154.32. Anal. Calcd for $C_{11}H_{11}N_{30}$ (201.23): C, 65.66; H, 5.51; N, 20.89. Found: C, 65.38; H, 5.51; N, 21.05.

EXAMPLE 2

3,4-dihydro-4-imino-3-allyl-2(1H)-quinazolinone

A mixture of 2-(3-allylureido)benzonitrile (10.0 g, 50 mmol) in ethanol (70 mL) and 28% of ammonia water (50 mL) was heated on a steam bath with occasional stirring for 15 minutes. The mixture was then cooled to room temperature and to the mixture was added water (100 mL). The solid was collected by filtration and was recrystallized from methanol with a few drops of ammonia water to give 8.4 g (84%) of 3,4-dihydro-4-imino-3-allyl-2(1H)-quinazolinone, mp 223°-224° C. IR (KBr): 3284, 3203, 3147, 1691, 1582 $cm^{-1}$. $^1H$ NMR (300 MHz, DMSO-d6): δ4.61 (d, 2H, =$CH_2$), 5.08 (q, 1H, $CH_2$), 5.85 (m, 1H, =CH), 7.07 (m, 2H, Ar—H), 7.46 (t, 1H, Ar—H), 8.04 (d, 1H, Ar—H), 8.85 (br s, 1H, NH), 10.74 (s, 1H, NH). $^{13}C$ NMR (75 MHz, DMSO-d6): δ42.54, 115.08, 115.81, 122.09, 126.13, 132.77, 133.15, 137.01, 149.76. Anal. Calcd for $C_{11}H_{11}N_3O$; C, 65.63; H, 5.56; N, 20.87. Found: C, 65.67; H, 5.51; N, 20.86.

EXAMPLE 3

2-Bromomethyl-2,3-dihydroimidazo[1,2-c]quinazolin-5(6H)-one

Method A: To a solution of 3,4-dihydro-4-imino-3-allyl-2(1H)-quinazolinone (10 g, 50 mmol) in tetrahydrofuran (70 mL) was added N-bromosuccinimide (9.0 g, 50 mmol). The mixture was then stirred at room temperature for 25 minutes. The solid was collected by filtration and recrystallized from THF to afford 2-bromomethyl-2,3-dihydro-imidazo[1,2-c]quinazolin-5(6H)-one (11.18 g, 95%), mp 213°-214° C. $^1$H NMR (300 MHz, DMSO-d6): δ3.67(m, 2H, CH$_2$), 3.74 (q, 1H, CH), 3.94 (t, 1H, CH), 4.57 (m, 1H, =CH), 7.07 (q, 2H, Ar—H), 7.51 (t, 1H, Ar—H), 7.78 (d, 1H, Ar—H), 10.65 (s, 1H, NH). $^{13}$C NMR (75 MHz, DMSO-d6): d 47.80, 64.16, 110.27, 115.13, 122.23, 125.80, 133.59, 139.97, 147.47, 153.98, 206.07. Anal. Calcd for $C_{11}H_{10}N_3OBr$: C, 47.16; H, 3.59; N, 15.00. Found: C, 47.09; H, 3.41; N, 14.90.

Method B: To a solution of 3,4-dihydro-4-imino-3-allyl-2(1H)-quinazolinone (0.5 g, 2.5 mmol) in dimethylsulfoxide (2.5 mL) and water (1 mL) was added N-bromosuccinimide (0.87 g, 5.0 mmol). The mixture was allowed to stir at room temperature and then was quenched with water (100 mL) to get solid. The solid was collected by filtration and washed with water to give 2-bromomethyl-2,3-dihydroimidazo[1,2-c]quinazolin-5(6H)-one (450 mg, 64%).

Method C: To a suspension of 3,4-dihydro-4-imino-3-allyl-2(1H)-quinazolinone (0.5 g, 2.5 mmol) in water (30 mL) was added N-bromosuccinimide (443 mg, 2.5 mmol). The mixture was allowed to stir at room temperature for 30 minutes. The solid was collected by filtration and washed with water (10 mL) to afford 2-bromomethyl-2,3-dihydroimidazo[1,2-c]quinazolin-5(6H)-one (680 mg, 97%).

EXAMPLE 4

2-(4-phenyl-1-piperazinyl)methyl-2,3-dihydroimidazo[1,2-c]quinazolin-5(6H)-one A mixture of 2-bromomethyl-2,3-dihydroimidazo[1,2-c]-quinazolin-5(6H)-one (0.5 g, 1.78 mmol), N-phenylpiperazine (0.28 mL, 3.56 mmol) in acetonitrile (25 mL) was refluxed for 13 hours. The hot mixture was filtered and washed with acetonitrile (10 mL) to give 2-(4-phenyl-1-piperazinyl)methyl-2,3-dihydroimidazo[1,2-c]-quinazolin-5(6H)-one (490 mg, 76%). An analytical sample was prepared from a mixture of acetonitrile and methanol (1:1), mp 257°-258° C. ms: m/z 361 (M+). $^1$H NMR (300 MHz, DMSO-d6): δ2.43-2.73 (m, 7H, CH$_2$), 3.11 (t, 3H, CH$_2$), 3.65 (q, 1H, CH), 3.91 (t, 1H, CH), 4.41 (m, 1H, CH), 6.75 (t, 1H, Ar—H), 6.91 (d, 2H, Ar—H), 7.06 (q, 2H, Ar—H), 7.17 (q, 2H, Ar—H), 7.48 (p, 1H, Ar—H), 7.78 (d, 1H, Ar—H), 10.53 (s, 1H, NH). Anal. Calcd for $C_{21}H_{23}N_5O$: C, 69.78; H, 6.41; N, 19.38. Found: C, 69.79; H, 6.45; N, 19.37.

EXAMPLE 5

3-{2,3-dihydroimidazo[1,2-c]quinazolin-5(6H)-one-2-yl}methyl-azaspiro-[5,5]undecane was obtained in 73% yield using a procedure similar to that which described in Example 4, mp 203°-205° C., ms: m/z 166 (M+), $^1$H NMR (300 MHz, DMSO-d6): δ1.27(s, 4H, CH$_2$), 1.34(s, 6H, CH$_2$), 2.28 (d, 2H, CH$_2$), 2.48 (d, 2H, CH$_2$), 3.39 (m, 7H, CH$_2$), 3.85 (t, 1H, CH), 4.34 (m, 1H, CH), 7.03 (m, 2H, Ar—H), 7.47 (t, 1H, Ar—H), 7.74 (d, 1H, Ar—H), 10.54 (s, 1H, NH). Anal. Calcd for $C_{21}H_{28}N_4O$: C, 71.56; H, 8.01; N, 15.90. Found; C, 71.50; H, 8.02; N, 15.89.

EXAMPLE 6

2-[4-piperonyl-1-piperazinyl]methyl-2,3-dihydroimidazo[1,2-c]-quinazolin-5(6H)-one

A mixture of 2-bromomethyl-2,3-dihydroimidazo[1,2-c]-quinazolin-5(6H)-one (0.5 g, 1.78 mmol), 1-piperonylpiperazine (0.78 g, 3.56 mmol) in acetonitrile (25 mL) was refluxed for 17 hours. The solvent was then removed in vacuo to the oily residue. The residue was purified by column chromatography [silica gel: 25 g, column diameter: 2.5 cm, solvent system: chloroform/ethylacetate (9/1)] to furnish 2-[4-piperonyl-1-piperazinyl]methyl-2,3-dihydroimidazo[1,2-c]-quinazolin-5(6H)-one hydrobromide (620 mg, 67%) and 2-methyl-2,3-dihydroimidazo[1,2-c]quinazolin-5(6H)-one (90 mg, 22%). 2-[4-piperonyl-1-piperazinyl]methyl-2,3-dihydroimidazo[1,2-c]-quinazolin-5(6H)-one hydrobromide: mp 236°-238° C. Anal.

Calcd for $C_{23}H_{23}N_5O_3/H_2O/HBr$: C, 53.29; H, 5.44; N, 13.50. Found: C, 53.45; H, 5.46; N, 13.54.

2-methyl-2,3-dihydroimidazo[1,2-c]quinazolin-5(6H)-one $^1H$ NMR (300 MHz, DMSO-d6): δ2.32 (s, 3H, $CH_3$), 7.27 (t, 1H, Ar—H), 7.35 (d, 1H, Ar—H), 7.57 (s, 1H, Ar—H), 8.10 (d, 1H, Ar—H). Anal. Calcd for $C_{11}H_9N_3O$: C, 66.32; H, 4.55; N, 21.09. Found: C, 66.37; H, 4.56; N, 21.09.

EXAMPLE 7

2-[4-(2-methoxy)phenyl-1-piperazinyl]methyl-2,3-dihydroimidazo[1,2-c]-quinazolin-5(6H)-one was obtained in 66% yield using a procedure similar to that which described in Example 4, mp 226°–227° C. ms: m/z 391 (M+). $^1H$ NMR (300 MHz, DMSO-d6): δ2.44–2.69 (m, 6H, $CH_2$), 2.95 (br s, 4H, $CH_2$), 3.67 (q, 1H, CH), 3.76 (s, 3H, O—$CH_3$), 3.87 (t, 1H, CH), 4.40 (m, 1H, CH), 6.88 (d, 4H, Ar—H), 7.06 (m, 2H, Ar—H), 7.48 (t, 1H, Ar—H), 7.78 (d, 1H, Ar—H), 10.50 (br s, 1H, NH). Anal. Calcd for $C_{22}H_{25}N_5O_2$: C, 67.50; H, 6.44; N, 17.89. Found: C, 67.54; H, 6.44; N, 17.90.

EXAMPLE 8

2-[4-Benzyl-1-piperazinyl]methyl-2,3-dihydroimidazo[1,2-c]quinazolin-5(6H)-one was obtained in 64% yield using a procedure similar to that which described in Example 4, mp 222°–224° C. $^1H$ NMR (300 MHz, DMSO-d6): δ2.50–3.00 (br s, 10H, $CH_2$), 3.74–3.80 (br s, 3H, $CH_2$), 4.04 (t, 1H, CH), 4.53 (m, 1H, CH), 6.99–7.10 (m, 2H, Ar—H), 7.24–7.41 (m, 6H, Ar—H), 7.90 (d, 1H, Ar—H), 9.15 (br s, 1H, NH). Anal. Calcd for $C_{22}H_{25}N_5O$: C, 70.38; H, 6.71; N, 18.65. Found: C, 70.39; H, 6.67; N, 18.68.

EXAMPLE 9

2-[4-Benzyl-1-piperidinyl]methyl-2,3-dihydroimidazo[1,2-c]quinazolin-5(6H)-one was obtained in 62% yield using a procedure similar to that which described in Example 4, mp 225°–227° C. $^1H$ NMR (300 MHz, DMSO-d6): δ1.56–1.66 (br s, 5H, $CH_2$), 2.21–2.33 (br s, 2H, $CH_2$), 2.54 (br s, 2H, CH), 2.75 (br s, 1H, CH), 2.90 (br s, 1H, CH), 3.09 (br s, 1H, CH), 3.29 (br s, 1H, CH), 3.80 (q, 1H, CH), 4.06 (t, 1H, CH), 4.60 (m, 1H, CH), 6.99–7.29 (m, 7H, Ar—H), 7.39 (t, 1H, Ar—H), 7.89 (d, 1H, Ar—H), 9.49 (br s, 1H, NH). Anal. Calcd for $C_{23}H_{26}N_4O$: C, 73.77; H, 7.00; N, 14.96. Found: C, 73.64; H, 7.02; N, 15.02.

EXAMPLE 10

2-[4-(2-Pyridinyl)-1-piperazinyl]methyl-2,3-dihydroimidazo[1,2-c]-quinazolin-5(6H)-one was obtained in 81% yield using a procedure similar to that which described in Example 4, mp 242°–243° C. $^1H$ NMR (300 MHz, DMSO-d6): δ2.65–2.83 (br s, 6H, $CH_2$), 3.59 (br s, 4H, $CH_2$), 3.91 (q, 1H, CH), 4.09 (t, 1H, CH), 4.57 (m, 1H, CH), 6.62 (t, 2H, Ar—H), 6.98 (d, 1H, Ar—H), 7.11 (t, 1H, Ar—H), 7.45 (q, 2H, Ar—H), 7.95 (d, 1H, Ar—H), 8.17 (d, 1H, Ar—H), 9.04 (br s, 1H, NH). Anal Calcd for $C_{20}H_{22}N_6O$: C, 66.28; H, 6.12; N, 23.19. Found: C, 66.23; H, 6.10; N, 23.1.

EXAMPLE 11

2-[4-(4-fluorobenzyl)-1-piperazinyl]methyl-2,3-dihydroimidazo[1,2-c]-quinazolin-5(6H)-one was obtained in 61% yield using a procedure similar to that which described in Example 4, mp 248°–249° C. Anal. Calcd for $C_{21}H_{22}N_5OF$: C, 66.48; H, 5.84; N, 18.46. Found: C, 66.54; H, 5.85; N, 18.49.

EXAMPLE 12

2-[1-benzylpiperidin-4-yl]aminomethyl-2,3-dihydroimidazo[1,2-c]-quinazolin-5(6H)-one was obtained in 76% yield using a procedure similar to that which described in Example 4, mp 206°-208° C. Anal. Calcd for $C_{23}H_{27}N_5O$: C, 70.93; H, 6.99; N, 17.98. Found: C, 70.71; H, 6.87; N, 17.97.

EXAMPLE 13

8-{2,3-dihydroimidazo[1,2-c]quinazolin-5(6H)-one-2-yl}methyl-1-phenyl-1,3,8-triazaspiro[4,5]decan-4-one was obtained in 74% yield using a procedure similar to that which described in Example 4, mp 250°-251° C. (acetonitrile); $^1$H NMR (300 MHz, DMSO-d6): δ1.52 (q, 2H, CH$_2$), 2.44-2.64 (m, 4H, 2 CH$_2$), 2.78-2.89 (m, 4H, 2CH$_2$), 3.71-3.77 (m, 1H, CH), 3.96 (m, 1H, CH), 4.37 (m, 1H, CH), 4.55 (s, 2H, CH$_2$), 6.71-6.82 (m, 3H, Ar—H), 7.06 (t, 2H, Ar—H), 7.22 (t, 2H, Ar—H), 7.46 (t, 1H, Ar—H), 7.77 (d, 1H, Ar—H), 8.59 (s, 1H, NH), 10.54 (s, 1H, NH). Anal. Calcd for $C_{24}H_{26}N_6O_2$·½H$_2$O (430.508): C, 66.27; H, 6.14; N, 19.32. Found: C, 66.32; H, 6.14; N, 19.21

EXAMPLE 14

2-[1-(4-chlorobenzhydryl)piperazinyl]methyl-2,3-dihydroimidazo[1,2-c]-quinazolin-5(6H)-one was obtained in 40% yield using a procedure similar to that which described in Example 4, mp 245°-246° C. (acetonitrile); $^1$H NMR (300 MHz, DMSO-d6): δ2.29-2.57 (m, 10H, CH$_2$), 3.29 (m, 1H, CH), 3.59 (m, 1H, CH), 3.84 (t, 1H, CH), 4.31 (s, 2H, CH$_2$), 7.01-7.75 (m, 13H, Ar—H), 10.50 (br s, 1H, NH). Anal. Calcd for $C_{28}H_{29}N_5OCl$ (486.015): C, 69.20; H, 5.81; N, 14.40. Found: C, 68.85; H, 5.84; N, 14.26.

EXAMPLE 15

2-[1-(4-p-fluorobenzoyl)piperidinyl]methyl-2,3-dihydroimidazo[1,2-c]-quinazolin-5(6H)-one was obtained in 81% yield using a procedure similar to that which described in Example 4, mp 220°-221° C. (acetone); $^1$H NMR (300 MHz, DMSO-d6): δ1.51-1.73 (m, 4H, 2 CH$_2$), 2.10-2.42 (m, 5H, 2 CH$_2$+CH), 2.87 (d, 1H, CH), 3.06 (d, 1H, CH), 3.36 (m, 1H, CH), 3.62 (m, 1H, CH), 3.88 (m, 1H, CH), 4.37 (m, 1H, CH), 7.06 (m, 2H, Ar—H), 7.33 (m, 2H, Ar—H), 7.76 (d, 1H, Ar—H), 8.04 (m, 2H, Ar—H), 10.50 (s, 1H, NH).

EXAMPLE 16

2-[1-(4-methoxyphenyl)piperazinyl]methyl-2,3-dihydroimidazo[1,2-c]-quinazolin-5(6H)-one was obtained in 54% yield using a procedure similar to that which described in Example 4, mp 229°-231° C. (CH$_3$CN); $^1$H NMR (300 MHz, DMSO-d6): δ2.42-2.71 (m, 6H, 3CH$_2$), 3.09 (m, 4H, 2CH$_2$), 3.65 (m, 1H, CH), 3.69 (s, 3H, CH$_3$), 3.90 (m, 1H, CH), 4.41 (m, 1H, CH), 6.33-6.51 (m, 3H, Ar—H), 7.03-7.11 (m, 3H, Ar—H), 7.48 (t, 1H, Ar—H), 7.78 (d, 1H, Ar—H), 10.50 (s, 1H, NH); ms; m/z 391 (M+), 229, 205. Anal. Calcd for $C_{22}H_{25}N_5O_2$ (391.475): C, 67.50; H, 6.44; N, 17.89. Found: C, 67.67; H, 6.36; N, 17.82.

EXAMPLE 17

2-[1-(3-methoxyphenyl)piperazinyl]methyl-2,3-dihydroimidazo[1,2-c]-quinazolin-5(6H)-one was obtained in 88% yield using a procedure similar to that which described in Example 4, mp>300° C. Anal. Calcd for $C_{22}H_{25}N_5O_2$ (391.475): C, 67.50; H, 6.44; N, 17.89. Found: C, 67.47; H, 6.31; N, 17.72.

EXAMPLE 18

3,4-dihydro-4-imino-3-allyl-quinazolin-2(1H)-thione

A mixture of anthranilonitrile (10.0 g, 85 mmol) and allyl isothiocyanate (15 mL, 151 mmol) was slightly heated to dissolve. The resulting solution was allowed to stir at room temperature for five days. The solid was collected by filtration and washed with acetonitrile (10 mL), and was recrystallized from ethanol to give 8.05 g (44%) of 3,4-dihydro-4-imino-3-allyl-quinazolinone-2(1H)-thione, mp 168°-169° C. $^1$H NMR (300 MHz, DMSO-d6): δ5.07-5.25 (m, 4H, =CH$_2$+CH$_2$), 5.75-6.06 (m, 1H, =CH), 7.13-7.63 (m, 3H, Ar—H), 8.05-8.13 (d, 1H, Ar—H), 9.40 (s, 1H, NH), 12.13 (s, 1H, NH). $^{13}$C-NMR (75 MHz, DMSO-d6): δ48.43, 115.56, 116.63, 123.92, 125.96, 132.20, 133.04, 135.59, 174.38. ms: m/z, 217 (M+), 201, 183, 160. Anal. Calcd for C$_{11}$H$_{11}$N$_3$S (217.29); C, 60.80; H, 5.10; N, 19.34. Found: C, 60.95; H, 5.13; N, 19.34.

EXAMPLE 19

2-bromomethyl-2,3-dihydroimidazo[1,2-c]quinazolin-5(6H)-thione

To a solution of 3,4-dihydro-4-imino-3-allyl-quinazolin-2(1H)-thione (5.5 g, 25.31 mmol) in acetonitrile (60 mL) was added N-bromosuccinimide (6.0 g, 33.52 mmol). The mixture was then stirred at room temperature for 50 minutes. The solid was collected by filtration and recrystallized from a mixture of acetonitrile and methanol to afford 2-bromomethyl-2,3-dihydro-imidazo[1,2-c]-quinazolin-5(6H)-thione (3.01 g, 40%), mp>300° C. $^1$H NMR (300 MHz, DMSO-d6): δ3.90(m, 2H, CH$_2$), 4.54-4.73(m, 3H, CH & CH$_2$), 7.66.7.71 (t, 2H, Ar—H), 7.97-9.02 (m, 1H, Ar—H), 8.54 (d, 1H, Ar—H), 9.80 (s, 1H, NH), 10.50 (s, 1H, NH). $^{13}$C-NMR (100 MHz, DMSO-d6): δ47.80, 64.16, 110.27, 115.13, 122.23, 125.80, 133.59, 139.97, 147.47, 153.98, 206.07. ms:m/z, 296 (M+), 295 (M+-1), 216(M+-80), 202(M+-94). Anal. Calcd for C$_{11}$H$_{10}$N$_3$SBr.HBr (377.10): C, 35.04; H, 2.94; N, 11.14. Found: C, 35.14; H, 3.01; N, 10.94.

EXAMPLE 20

2-(4-phenyl-1-piperazinyl)methyl-2,3-dihydroimidazo[1,2-c]quinazolin-5(6H)-thione A mixture of 2-bromomethyl-2,3-dihydroimidazo[1,2-c]quinazolin-5(6H)-thione (3.0 g, 10.13 mmol), N-phenylpiperazine (2.5 mL, 15.41 mmol) and sodium bicarbonate (1.7 g, 20.24 mmol) in acetonitrile (70 mL) was refluxed for 24 hours. The hot mixture was filtered and washed with acetonitrile (10 mL) to give 2-(4-phenyl-1-piperazinyl)methyl-2,3-dihydroimidazo[1,2-c]-quinazolin-5(6H)-thione (490 mg, 76%). An analytical sample was prepared from a mixture of acetonitrile and methanol (1:1), mp 257°-258° C. ms:m/z 361 (M+). $^1$H NMR (300 MHz, DMSO-d6): δ2.43-2.73 (m, 7H, CH$_2$), 3.11 (t, 3H, CH$_2$), 3.65 (q, 1H, CH), 3.91 (t, 1H, CH), 4.41 (m, 1H, CH), 6.75 (t, 1H, Ar—H), 6.91 (d, 2H, Ar—H), 7.06 (q, 2H, Ar—H), 7.17 (q, 2H, Ar—H), 7.48 (p, 1H, Ar—H), 7.78 (d, 1H, Ar—H), 10.53 (s, 1H, NH). $^{13}$C NMR (75 MHz, DMSO-d6): δ29.43, 48.14, 51.91, 52.67, 61.18, 115.33, 118.75, 124.75, 124.92, 125.60, 128.81, 132.41, 145.39, 150.86, 159.50, 179.22.

EXAMPLE 21

2-nitro-4,5-dimethoxybenzonitrile

To a nitric acid (40 mL) in ice bath was added 3,4-dimethoxybenzonitrile (5.0 g, 30.6 mmol) and was allowed to stir for 2 hours. Then the solution was gradually returned to room temperature. To this solution was added ice (200 mL) to get light yellow precipitate which was then collected by filtration to give 6.25 g (98%) of 2-nitro-4,5-dimethoxybenzonitrile. $^1$H NMR (100 MHz, DMSO-d6): δ3.69 (s, 3H, CH$_3$), 3.90 (s, 3H, CH$_3$), 7.53 (s, 1H, Ar—H), 7.75 (s, 1H, Ar—H). ms: m/z 208 (M+), 192 (M+-16), 178 (M+-30), 162 (M+-46).

EXAMPLE 22

2-amino-4,5-dimethoxybenzonitrile

A suspension of 2-nitro-4,5-dimethoxybenzonitrile (6.0 g, 28.8 mmol) in water (200 mL) was heated to 90° C. To this hot mixture was added sodium dithionite in a small portion until it was dissolved completely. The resulting solution was filtered and then cooled to room temperature to get crystal. The solid was collected by filtration to afford 4.99 g (97%) of 2-amino-4,5-dimethoxybenzonitrile. An analytical sample was recrystallized from acetonitrile. $^1$H NMR (100 MHz, DMSO-d6): δ3.64 (s, 3H, CH$_3$), 3.73 (s, 3H, CH$_3$), 4.32 (br s, 2H, NH$_2$), 6.41 (s, 1H, Ar—H), 6.86 (s, 1H, Ar—H). $^{13}$C NMR (25 MHz, DMSO-d6): d 55.55, 56.87, 83.67, 92.08, 113.96, 140.33, 148.12, 154.33. MS: m/z 178 (M+), 163 (M+-15), 147 (M+-31), 135 (M+-43), 120 (M+-58).

EXAMPLE 23

3,4-dihydro-3-allyl-4-imino-6,7-dimethoxyquinazolin-2(H)-one was prepared in 72% yield using a similar procedure which described in Example 2. An analytical sample was recrystallized from ethanol. 1H NMR (100 MHz, DMSO-d6): δ3.78 (s, 6H, 2(CH₃)), 4.62 (d, 2H, J=4.8 Hz, CH₂), 5.05 (d, 2H, J=12.8 Hz, CH₂), 5.94–6.03 (m, 1H, CH), 6.62 (s, 1H, Ar—H), 7.54 (s, 1H, Ar—H). ms: m/z 260 (M+-1), 246 (M+-15), 230 (M+-31), 216 (M+-45), 206 (M+-55).

EXAMPLE 24

2-bromomethyl-8,9-dimethoxy-2,3-dihydroimidazo[1,2-c]quinazolin-5(6H)-one was prepared in 92% yield using a similar procedure as described in Example 3. ¹H NMR (100 MHz, DMSO-d6): δ3.78 (s, 3H, CH₃), 3.83 (s, 3H, CH₃), 3.78–4.21 (m, 4H, 2 (CH₂)), 6.68 (s, 1H, Ar—H), 7.32 (s, 1H, Ar—H). MS: m/z 341 (M+), 259 (M+-82), 246 (M+-95).

EXAMPLE 25

2-(4-phenyl-1-piperazinyl)methyl-8,9-dimethoxy-2,3-dihydro-imidazo-[1,2-c]quinazolin-5(6H)-one was obtained in 90% yield using a procedure similar to that which described in Example 4. An analytical sample was recrystallized from ethanol, mp 283°–284° C., ms: m/z 421 (M+), 303 (M+-118), 289 (M+-132), 275 (M+-146). ¹H NMR (100 MHz, DMSO-d6+1N D₂SO₄): δ3.37 (brs, 8H, 4(CH₂)), 3.81 (s, 3H, CH₃), 3.88 (s, 3H, CH₃), 3.62–4.20 (m, 3H, CH₂+CH), 4.46 (t, 1H, CH), 4.95 (br s, 1H, CH), 6.79 (s, 1H, Ar—H), 6.82–7.23 (m, 5H, Ar—H), 7.56 (s, 1H, Ar—H). ¹³C-NMR (25 MHz, DMSO-d6+1N D₂SO₄): δ46.35, 49.70, 52.15, 52.50, 56.78, 57.19, 58.82, 96.33, 98.55, 107.05, 116.66, 121.11, 130.22, 141.02, 146.02, 146.66, 148.53, 158.37, 158.55. Anal. Calcd for C₂₃H₂₇N₅O₃ (421.50): C, 65.54; H, 16.62; N, 6.46. Found: C, 65.33; H, 16.54; N, 6.51.

What is claimed is:

1. An imidazo[1,2-c]quinazoline compound having the formula which comprises racemic mixture of optically active compounds or optically pure R and S stereoisomers, wherein:

X is O or S;

R₁ is hydrogen, lower alkyl, phenyl or phenyl (lower alkyl);

R₂ is hydrogen, lower alkyl, phenyl or phenyl (lower alkyl); or R₁ and R₂ together represent alkylene of 4 to 10 carbon atoms or wherein R₅ represents (a) 2-(2-hydroxyethoxy)ethyl; (b) pyrimidinyl; (c) a 2-, 3- or 4-pyridinyl optionally substituted by one or two substituents each independently selected from the group consisting of C₁-C₄ alkyl; and (d) benzoyl, benzyl, phenyl and diphenylmethyl optionally substituted by one or two substituents selected from the group consisting of halogen atom, methoxy, trifluoromethyl, C₁-C₄ alkyl, nitro, acetyl, and cyano; and (i) R₆ and R₇ together represent alkylene of 4 to 6 carbon atoms or (ii)

or (iii) when R₆ represents hydrogen atom or hydroxy, R₇ represents (a) pyrimidinyl; (b) a 2-, 3- or 4-pyridinyl optionally substituted by one or two substituents each independently selected from the group consisting of C₁-C₄ alkyl; and (c) benzoyl, benzyl, phenyl and diphenylmethyl optionally substituted by one or two substituents selected from the group consisting of halogen atom, methoxy, trifluoromethyl, C₁-C₄ alkyl, nitro, acetyl, and cyano;

R₃ is halogen, hydrogen, lower alkyl, trifluoromethyl, or lower alkoxy; and

R₄ is halogen, hydrogen, lower alkyl, trifluoromethyl, or lower alkoxy; or pharmaceutically acceptable salts thereof.

2. A pharmaceutical composition for the treatment of hypertension, which comprises a therapeutically effective amount of an imidazo[1,2-c]quinazoline compound of the formula (I) as defined in claim 1 or a pharmaceutically acceptable salt thereof, as an active ingredient, in combination with a pharmaceutically acceptable carrier or diluent for the active ingredient.

3. A method for and treatment of hypertension comprising administrating to a mammal in need of such treatment a therapeutically effective amount of an imidazo[1,2-c]quinazoline compound of the formula (I) as defined in claim 1.

4. The compound according to claim 1, wherein said compound is 2-(4-phenyl-1-piperazinyl)-methyl-2,3-dihydroimidazo[1,2-c]quinazolin-5(6H)-one.

5. The pharmaceutical composition according to claim 2, wherein the imidazo[1,2-c]quinazoline compound is 2-(4-phenyl-1-piperazinyl)-methyl-2,3-dihydroimidazo[1,2-c]quinazolin-5(6H)-one.

6. The method according to claim 3 wherein the imidazo[1,2-c]quinazoline compound is 2-(4-phenyl-1-piperazinyl)-methyl-2,3-dihydroimidazo[1,2-c]quinazolin-5(6H)-one.

7. The compound according to claim 1, wherein said compound is 2-(4-phenyl-1-piperazinyl)-methyl-2,3-dihydroimidazo[1,2-c]quinazolin-5(6H)-thione.

8. The pharmaceutical composition according to claim 2, wherein the imidazo[1,2-c]quinazoline compound is 2-(4-phenyl-1-piperazinyl)-methyl-2,3-dihydroimidazo[1,2-c]quinazolin-5(6H)-thione.

9. The method according to claim 3 wherein the imidazo[1,2-c]quinazoline compound is 2-(4-phenyl-1-piperazinyl)-methyl-2,3-dihydroimidazo[1,2-c]quinazolin-5(6H)-thione.

10. The compound according to claim 1, wherein said compound is 2-(4-phenyl-1-piperazinyl)-methyl-8,9-dimethoxy-2,3-dihydro-imidazo[1,2-c]quinazolin-5(6H)-one.

11. The pharmaceutical composition according to claim 2, wherein the imidazo[1,2-c]quinazoline compound is 2-(4-phenyl-1-piperazinyl)-methyl-8,9-dimethoxy-2,3-dihydro-imidazo[1,2-c]quinazolin-5(6H)-one.

12. The method according to claim 3, wherein the imidazo[1,2-c]quinazoline compound is 2-(4-phenyl-1-piperazinyl)-methyl-8,9-dimethoxy-2,3-dihydro-imidazo[1,2-c]quinazolin-5(6H)-one.

* * * * *